United States Patent
Torii et al.

(10) Patent No.: US 11,813,095 B2
(45) Date of Patent: Nov. 14, 2023

(54) RADIATION IMAGING APPARATUS, RADIATION IMAGING METHOD, AND NON-TRANSITORY COMPUTER-READABLE STORAGE MEDIUM

(71) Applicant: CANON KABUSHIKI KAISHA, Tokyo (JP)

(72) Inventors: Sota Torii, Kanagawa (JP); Atsushi Iwashita, Tokyo (JP); Takeshi Noda, Kanagawa (JP); Kosuke Terui, Kanagawa (JP); Akira Tsukuda, Tokyo (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 343 days.

(21) Appl. No.: 17/127,302

(22) Filed: Dec. 18, 2020

(65) Prior Publication Data
US 2021/0118193 A1    Apr. 22, 2021

Related U.S. Application Data

(63) Continuation of application No. PCT/JP2019/018337, filed on May 8, 2019.

(30) Foreign Application Priority Data

Jun. 27, 2018  (JP) ................................ 2018-122352
Jun. 27, 2018  (JP) ................................ 2018-122354

(51) Int. Cl.
  *A61B 6/00*     (2006.01)
  *G01T 1/161*    (2006.01)
(Continued)

(52) U.S. Cl.
  CPC ............ *A61B 6/4241* (2013.01); *A61B 6/461* (2013.01); *A61B 6/482* (2013.01); *A61B 6/54* (2013.01);
(Continued)

(58) Field of Classification Search
None
See application file for complete search history.

(56) References Cited

U.S. PATENT DOCUMENTS 8,355,594 B2    1/2013 Noda et al.
8,655,034 B2    2/2014 Noda et al.
(Continued)

FOREIGN PATENT DOCUMENTS

JP    2011-172803 A    9/2011
JP    2012-210290 A    11/2012
(Continued)

OTHER PUBLICATIONS

U.S. Appl. No. 16/103,150, Atsushi Iwashita, filed Aug. 14, 2018.

*Primary Examiner* — Nancy Bitar
(74) *Attorney, Agent, or Firm* — VENABLE LLP

(57) ABSTRACT

A radiation imaging apparatus comprises a generating unit configured to generate a material characteristic image with respect to a plurality of materials included in a radiation image that has been captured using different radiation energies; and a reconstructing unit configured to set different radiation energies for the respective plurality of materials, and to generate a reconstructed image based on monochromatic radiation images of the respective materials, the monochromatic radiation images being based on the different radiation energies.

26 Claims, 10 Drawing Sheets

(51) Int. Cl.
  *G01T 1/17*    (2006.01)
  *G06F 18/22*   (2023.01)
  *G06V 10/98*   (2022.01)
  *G06T 7/00*    (2017.01)
  *G06T 11/00*   (2006.01)

(52) U.S. Cl.
  CPC .............. *G01T 1/161* (2013.01); *G01T 1/17* (2013.01); *G06F 18/22* (2023.01); *G06T 7/0012* (2013.01); *G06T 11/00* (2013.01); *G06V 10/993* (2022.01); *A61B 6/5258* (2013.01); *G06T 2207/10116* (2013.01); *G06T 2207/30004* (2013.01); *G06V 2201/03* (2022.01)

(56) References Cited

U.S. PATENT DOCUMENTS

| | | | |
|---|---|---|---|
| 8,744,210 | B2 | 6/2014 | Noda et al. |
| 8,923,589 | B2 | 12/2014 | Noda et al. |
| 9,014,450 | B2 | 4/2015 | Noda et al. |
| 9,048,154 | B2 | 6/2015 | Takenaka et al. |
| 9,128,196 | B2 | 9/2015 | Sato et al. |
| 9,134,432 | B2 | 9/2015 | Iwashita et al. |
| 9,234,966 | B2 | 1/2016 | Sugawara et al. |
| 9,423,512 | B2 | 8/2016 | Sato et al. |
| 9,445,030 | B2 | 9/2016 | Yagi et al. |
| 9,462,989 | B2 | 10/2016 | Takenaka et al. |
| 9,468,414 | B2 | 10/2016 | Ryu et al. |
| 9,470,800 | B2 | 10/2016 | Iwashita et al. |
| 9,470,802 | B2 | 10/2016 | Okada et al. |
| 9,532,759 | B2 | 1/2017 | Taguchi |
| 9,541,653 | B2 | 1/2017 | Iwashita et al. |
| 9,655,586 | B2 | 5/2017 | Yagi et al. |
| 9,737,271 | B2 | 8/2017 | Iwashita et al. |
| 9,812,474 | B2 | 11/2017 | Yagi et al. |
| 9,820,711 | B2 | 11/2017 | Tsukuda |
| 9,820,713 | B2 | 11/2017 | Noda et al. |
| 9,953,414 | B2 | 4/2018 | Noda et al. |
| 9,971,046 | B2 | 5/2018 | Ryu et al. |
| 9,980,685 | B2 | 5/2018 | Iwashita et al. |
| 9,989,656 | B2 | 6/2018 | Sato et al. |
| 10,009,990 | B2 | 6/2018 | Takenaka et al. |
| 10,070,082 | B2 | 9/2018 | Tsukuda |
| 10,197,684 | B2 | 2/2019 | Terui et al. |
| 10,274,612 | B2 | 4/2019 | Ishii et al. |
| 10,441,238 | B2 | 10/2019 | Terui et al. |
| 10,779,777 | B2 | 9/2020 | Terui et al. |
| 10,782,251 | B2 | 9/2020 | Sato et al. |
| 11,531,122 | B2 * | 12/2022 | Terui .................... G01T 1/20184 |
| 2010/0131885 | A1 * | 5/2010 | Licato .................... G16H 30/20 715/764 |
| 2013/0116554 | A1 | 5/2013 | Kaiser |
| 2013/0287260 | A1 * | 10/2013 | Taguchi ................ G06T 11/005 382/103 |
| 2014/0239186 | A1 | 8/2014 | Sato et al. |
| 2014/0321603 | A1 * | 10/2014 | Taguchi ................ A61B 6/405 378/5 |
| 2014/0361189 | A1 | 12/2014 | Kameshima et al. |
| 2016/0171648 | A1 * | 6/2016 | Thibault ............... G06T 11/008 382/131 |
| 2016/0270755 | A1 | 9/2016 | Takenaka et al. |
| 2018/0128755 | A1 | 5/2018 | Iwashita et al. |
| 2019/0179036 | A1 | 6/2019 | Takenaka et al. |
| 2019/0320993 | A1 | 10/2019 | Noda et al. |
| 2019/0349541 | A1 | 11/2019 | Iwashita et al. |
| 2020/0124749 | A1 | 4/2020 | Takenaka et al. |
| 2020/0150059 | A1 | 5/2020 | Torii et al. |
| 2020/0150286 | A1 | 5/2020 | Terui et al. |
| 2020/0155097 | A1 | 5/2020 | Torii et al. |
| 2020/0163630 | A1 | 5/2020 | Noda et al. |
| 2020/0211238 | A1 | 7/2020 | Iwashita et al. |
| 2020/0245441 | A1 | 7/2020 | Tsukuda et al. |
| 2021/0041584 | A1 | 2/2021 | Terui et al. |
| 2021/0055233 | A1 | 2/2021 | Noda et al. |
| 2021/0067715 | A1 | 3/2021 | Kosuge et al. |
| 2021/0128096 | A1 * | 5/2021 | Konno ................... A61B 6/482 |
| 2022/0076397 | A1 * | 3/2022 | Torii ........................ A61B 6/00 |

FOREIGN PATENT DOCUMENTS

| | | |
|---|---|---|
| JP | 2014-061286 A | 4/2014 |
| JP | 2016-193921 A | 11/2016 |
| WO | 2016/147844 A1 | 9/2016 |

\* cited by examiner

FIG. 5
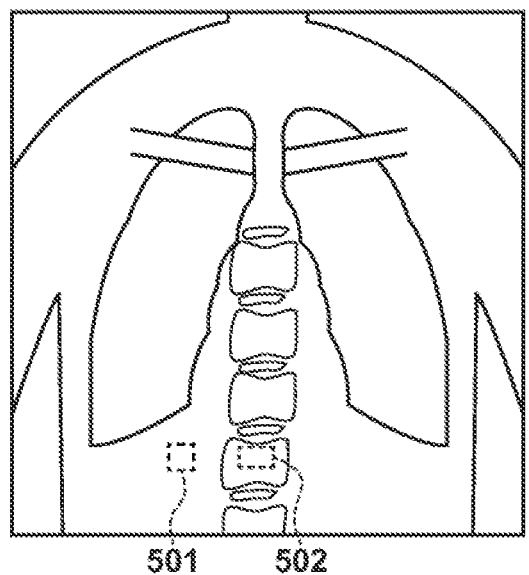
501  502
FIG. 6
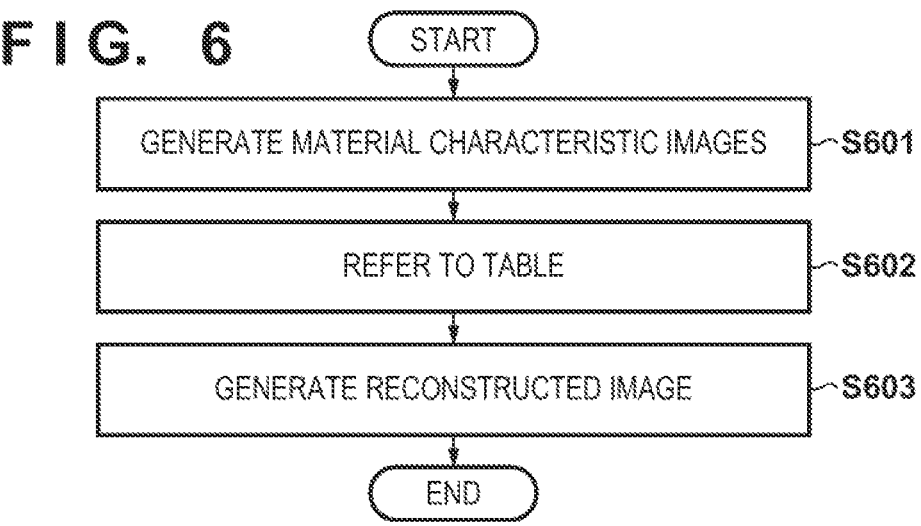
FIG. 7
| THICKNESS OF SUBJECT | E1 (keV) | E2 (keV) |
|---|---|---|
| THIN | 60 | 40 |
| MEDIUM | 70 | 40 |
| THICK | 80 | 40 |

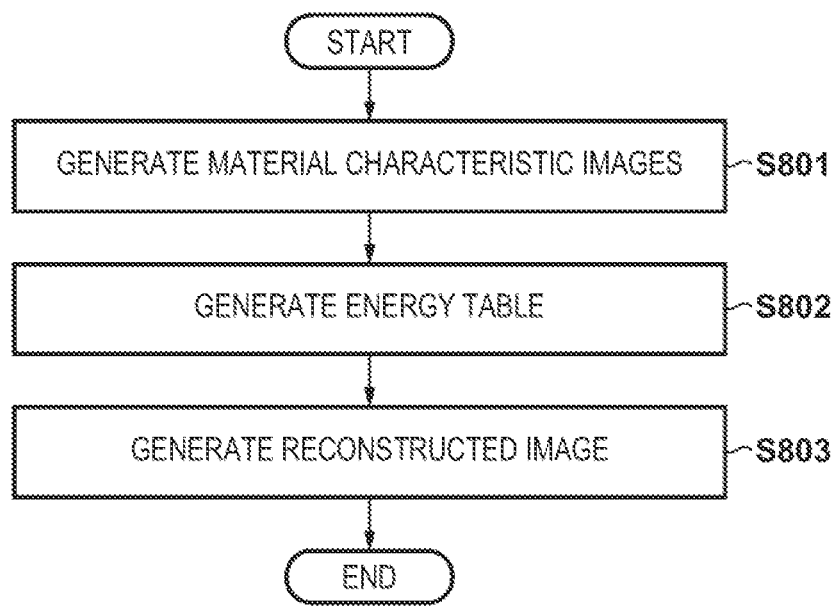
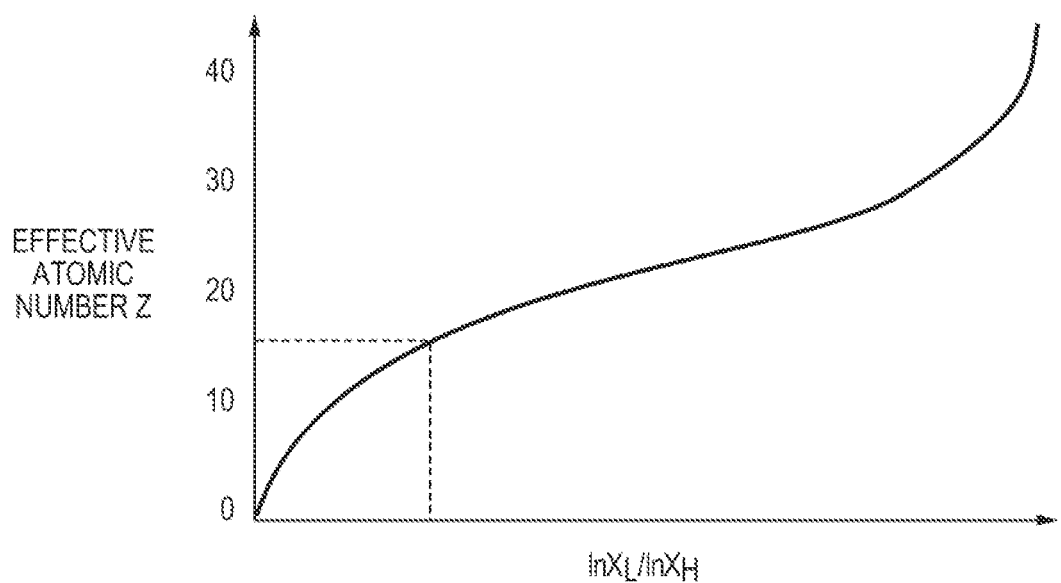

FIG. 10

| MATERIAL | EFFECTIVE ATOMIC NUMBER |
|---|---|
| FAT | 5.9~6.5 |
| WATER | 7.4 |
| MUSCLE | 7.4~7.6 |
| BONE | 12.3~13.8 |
| TITANIUM | 22 |
| STAINLESS | 26 |
| IODINE | 53 |
| BARIUM | 56 |

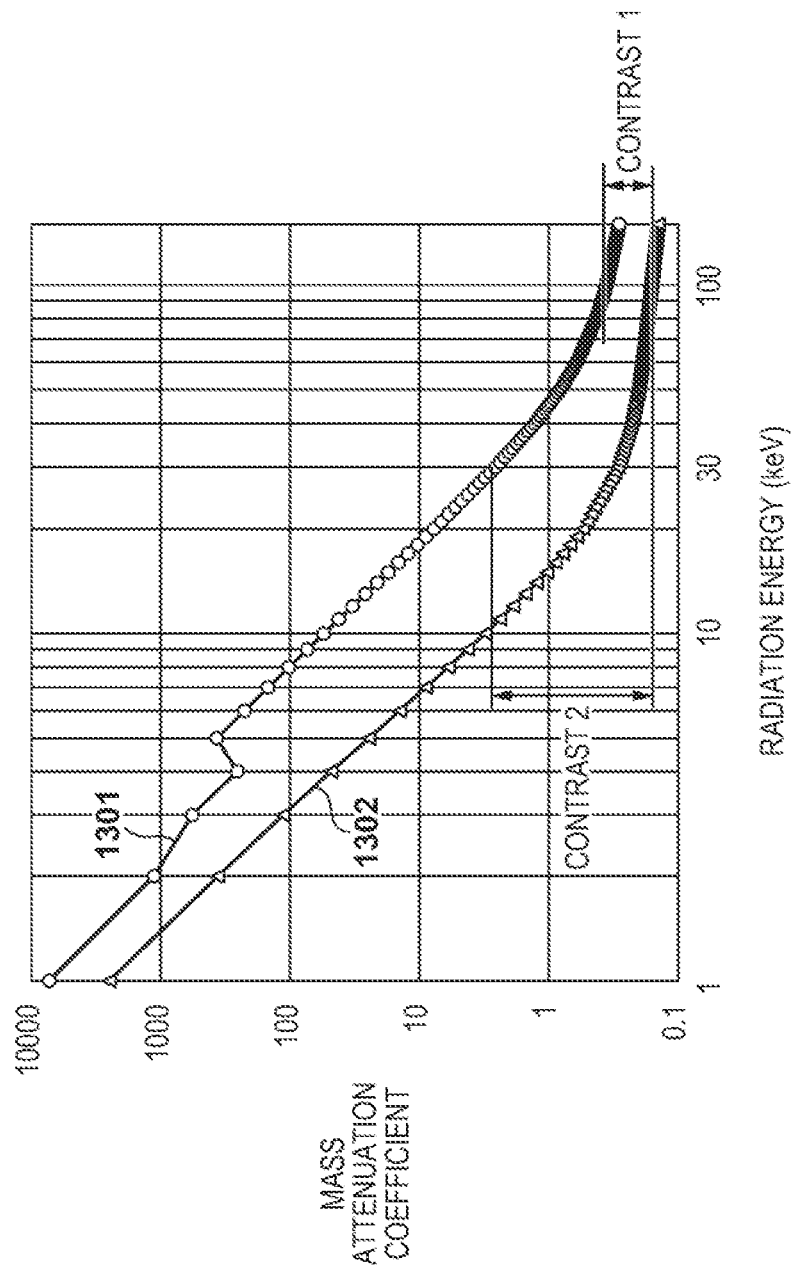

RADIATION IMAGING APPARATUS, RADIATION IMAGING METHOD, AND NON-TRANSITORY COMPUTER-READABLE STORAGE MEDIUM

CROSS-REFERENCE TO RELATED APPLICATIONS

This application is a Continuation of International Patent Application No. PCT/JP2019018337, filed May 8, 2019, which claims the benefit of Japanese Patent Application No. 2018-122352 and Patent Application No. 2018-122354, filed Jun. 27, 2018, which are hereby incorporated by reference herein in their entirety.

BACKGROUND OF THE INVENTION

Field of the Invention

The present invention relates to a radiation imaging apparatus, a radiation imaging method, and a non-transitory computer-readable storage medium.

Background Art

Radiation imaging apparatuses that use a flat panel detector (hereinafter abbreviated as "FPD") have become widespread as imaging apparatuses used in medical image diagnosis based on radiation. The FPD allows digital image processing to be performed with respect to a captured image; thus, for example, in medical image diagnosis, the FPD is used as a digital imaging apparatus that captures still images as in general imaging or captures moving images as in fluoroscopic imaging, or as a CT apparatus.

PTL 1 discloses a configuration that, on a CT apparatus, identifies materials by applying a method called dual energy scanning, in which a subject is imaged using two types of tube voltages, and generates a radiation image using appropriate radiation energy on a per-material basis.

CITATION LIST

Patent Literature

PTL1: Japanese Patent Laid-Open No. 2014-61286

However, the attenuation characteristics of radiation energy vary with each material; thus, in general imaging and fluoroscopic imaging that cannot obtain tomographic images, it is necessary to reconstruct a radiation image by setting radiation energy for each of a plurality of materials that exist on radiation beam lines.

The present invention provides a radiation imaging technique that enables reconstruction of a radiation image by setting different radiation energies for respective materials.

SUMMARY OF THE INVENTION

According to one aspect of the present invention, there is provided a radiation imaging apparatus, comprising:
a generating unit configured to generate a material characteristic image with respect to a plurality of materials included in a radiation image that has been captured using different radiation energies; and
a reconstructing unit configured to set different radiation energies for the respective plurality of materials, and generating a reconstructed image based on monochromatic radiation images of the respective materials, the monochromatic radiation images being based on the different radiation energies.

According to another aspect of the present invention, there is provided a radiation imaging apparatus, comprising:
an obtaining unit configured to obtain low-energy radiation distribution information and high-energy radiation distribution information that corresponds to a high energy level from a plurality of radiation images acquired through a single radiation irradiation from a radiation generating unit;
a generating unit configured to generate, from the low-energy radiation distribution information and the high-energy radiation distribution information, a material characteristic image in which a first material and a second material have been separated; and
a reconstructing unit configured to generate a reconstructed image based on a monochromatic radiation image based on first radiation energy corresponding to the first material and on a monochromatic radiation image based on second radiation energy corresponding to the second material.

Further features of the present invention will become apparent from the following description of exemplary embodiments with reference to the attached drawings.

BRIEF DESCRIPTION OF THE DRAWINGS

The accompanying drawings, which are incorporated in and constitute a part of the specification, illustrate embodiments of the invention and, together with the description, serve to explain principles of the invention.

FIG. 5 is a diagram exemplarily showing regions of interest for which an analysis value is to be acquired according to the first embodiment.

FIG. 6 is a diagram for describing a flow of processing in the image processing unit according to a second embodiment.

FIG. 7 is a diagram exemplarily showing a table for determining radiation energies according to the second embodiment.

FIG. 8 is a diagram for describing a flow of processing in the image processing unit according to a third embodiment.

FIG. 9 is a diagram showing a relationship between a logarithmic ratio between low-energy and high-energy radiation distribution information pieces and an effective atomic number Z.

FIG. 10 is a diagram exemplarily showing the effective atomic numbers of materials.

FIG. 13B is a diagram for describing the advantageous effects of the third embodiment.

DESCRIPTION OF THE EMBODIMENTS

Hereinafter, embodiments of the present invention will be exemplarily described in detail with reference to the drawings. Note, the constituent elements described in these embodiments are merely exemplary, and the technical scope of the present invention is determined by the claims and is not limited by the individual embodiments described below.

First Embodiment

Figure 1:
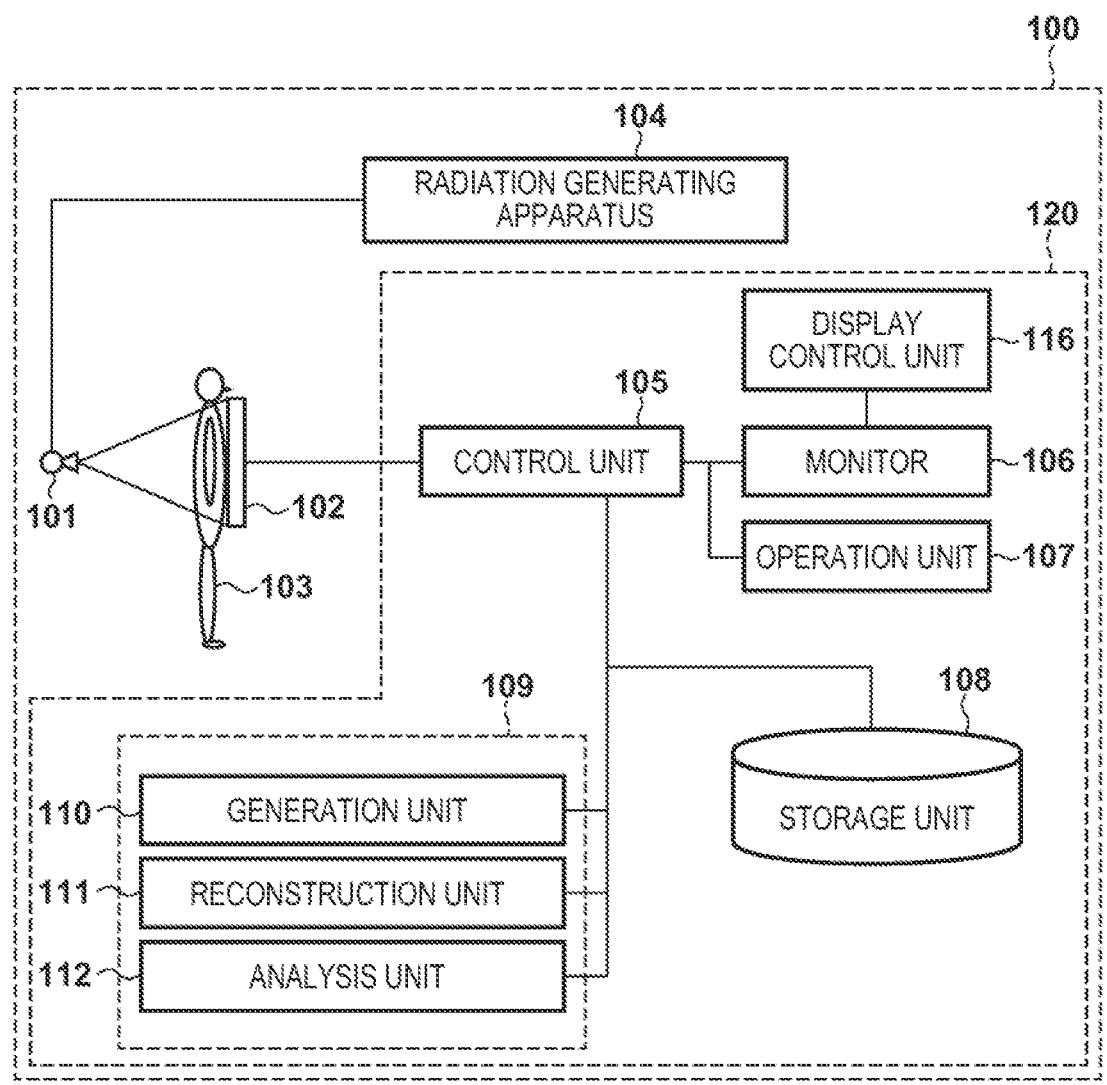
FIG. 1 is a diagram showing a configuration example of a radiation imaging system according to a first embodiment.

FIG. 1 is a diagram showing a configuration example of a radiation imaging system 100 according to a first embodiment of the present invention. The radiation imaging system 100 includes a radiation generating apparatus 104, a radiation source 101, an FPD 102 (a radiation detecting apparatus), and an information processing apparatus 120. Note that the configuration of the radiation imaging system 100 may be simply referred to as a radiation imaging apparatus. The information processing apparatus 120 processes information based on a radiation image obtained by imaging a subject.

When an irradiation switch is depressed, the radiation generating apparatus 104 generates radiation by applying a high-voltage pulse to the radiation source 101, and the radiation source 101 irradiates a subject 103 with radiation. Although the type of radiation is not limited in any particular way, X-rays can be used in general.

Once the subject 103 has been irradiated with radiation from the radiation source 101, the FPD 102 accumulates charges based on image signals, and obtains a radiation image. The FPD 102 transfers the radiation image to the information processing apparatus 120. Note that the FPD 102 may transfer the radiation image to the information processing apparatus 120 each time imaging is performed; the FPD 102 can also store images that have been captured into an image storage unit inside the FPD 102 without transferring the images on a per-imaging basis, and transfer the images collectively to the information processing apparatus 120 at a predetermined timing. Communication between the FPD 102 and the information processing apparatus 120 may be wired communication or wireless communication.

The FPD 102 includes a radiation detection unit (not shown) provided with a pixel array for generating signals corresponding to radiation. The radiation detection unit detects radiation that has been transmitted through the subject 103 as image signals. In the radiation detection unit, pixels that output signals corresponding to incident light are arranged in the form of an array (a two-dimensional region). A photoelectric conversion element of each pixel converts radiation, which has been converted into visible light by fluorescent materials, into an electrical signal, and outputs the electrical signal as an image signal. In this way, the radiation detection unit is configured to obtain image signals (a radiation image) by detecting radiation that has been transmitted through the subject 103. A driving unit of the FPD 102 outputs the image signals (radiation image) that have been read out in accordance with an instruction from a control unit 105 to the control unit 105.

The control unit 105 includes an image processing unit 109 that processes a radiation image obtained from the FPD 102, and a storage unit 108 that stores the result of image processing and various types of programs. The storage unit 108 is composed of, for example, a ROM (Read Only Memory), a RAM (Random Access Memory), and the like. The storage unit 108 can store images output from the control unit 105, images that have undergone image processing in the image processing unit 109, and the result of calculation in the image processing unit 109.

The image processing unit 109 includes a generation unit 110, a reconstruction unit 111, and an analysis unit 112 as functional constituents. With regard to these functional constituents, for example, the functions of each unit are configured using one or more CPUs (central processing units) and the programs that have been read from the storage unit 108. The functions of each unit of the image processing unit 109 may be configured using, for example, an integrated circuit as long as similar functions are achieved. Furthermore, the information processing apparatus 120 may be configured to include, as internal constituents, a graphic control unit such as a GPU (Graphics Processing Unit), a communication unit such as a network card, an input/output control unit such as a keyboard, a display, and a touchscreen, and so forth.

A monitor 106 (display unit) displays radiation images (digital images) that the control unit 105 has received from the FPD 102, and images that have undergone image processing in the image processing unit 109. A display control unit 116 can control display on the monitor 106 (display unit). An operation unit 107 can input instructions to the image processing unit 109 and the FPD 102, and accepts, as inputs, instructions to the FPD 102 via a user interface.

The control unit 105 can perform imaging control using an energy subtraction method, which acquires a new image (e.g., a bone image and a body fat image) by processing a plurality of radiation images obtained by irradiating the subject with different radiation energies. In performing imaging with use of the energy subtraction method, at least two radiation images that have been captured using different radiation energies are necessary to generate one subtraction image. The FPD 102 performs sampling multiple times with respect to a single radiation irradiation. In this way, the FPD 102 can obtain an image based on low-energy radiation (a low-energy radiation image) and an image based on high-energy radiation (a high-energy radiation image) through a single radiation irradiation. Imaging performed by the FPD 102 may be capturing of still images or capturing of moving images.

Figure 3:
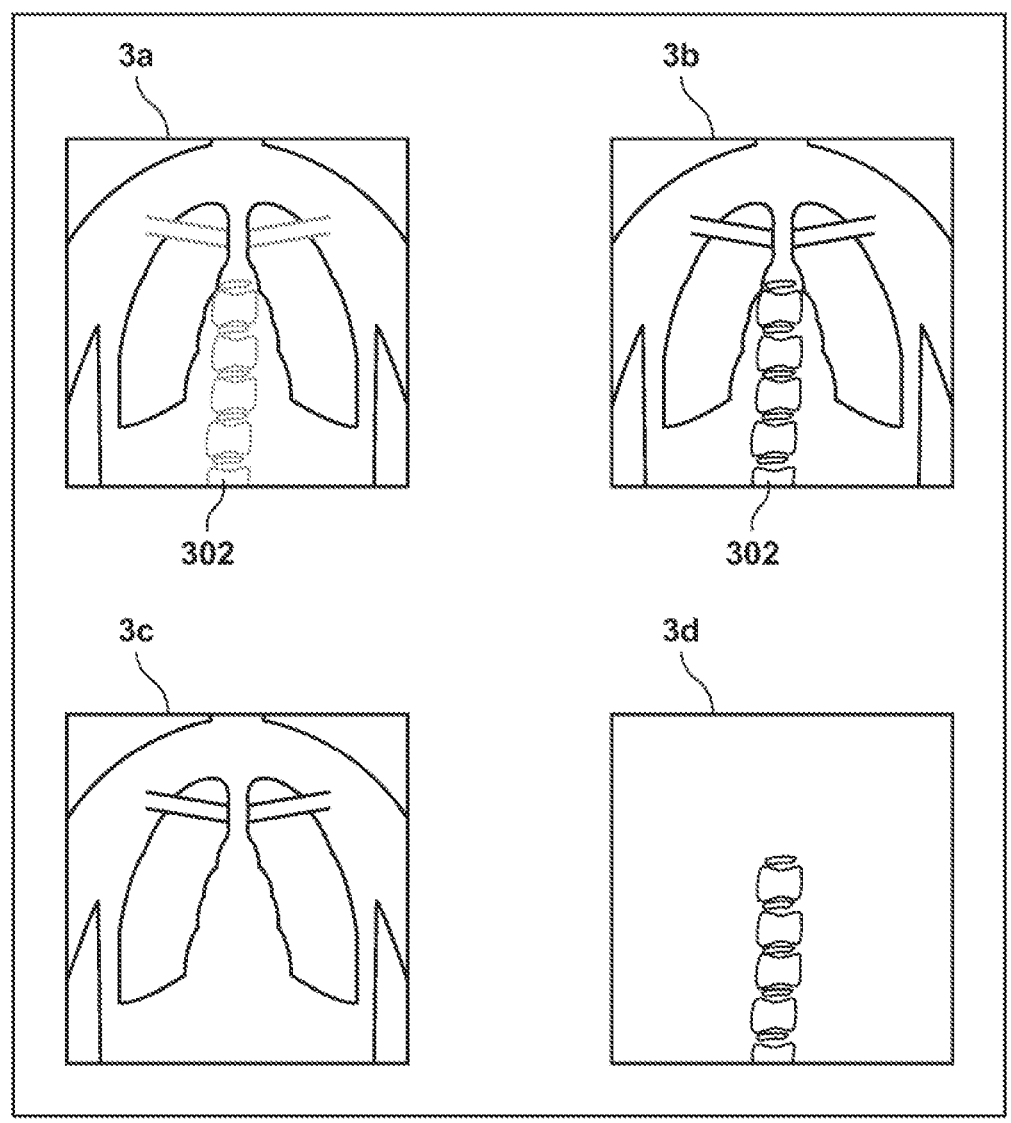
FIG. 3 presents 3a as a diagram exemplarily showing a high-energy radiation image, 3b as a diagram exemplarily showing a low-energy radiation image, 3c as a diagram exemplarily showing a material separation image of body fat, and 3d as a diagram exemplarily showing a material separation image of bones.

Radiation distribution information that has been temporarily stored in the FPD 102 can be read out after the execution of sample and hold, and the control unit 105 reads out radiation distribution information ($X_L$) and radiation distribution information ($X_L+X_H$) from the FPD 102 at different timings. The control unit 105 can acquire radiation distribution information ($X_H$) by subtracting the radiation distribution information ($X_L$) from the radiation distribution information ($X_L+X_H$). Here, the low-energy radiation distribution information ($X_L$) is an image that serves as a basis for a low-energy radiation image, and the high-energy radiation distribution information ($X_H$) is an image that serves as a basis for a high-energy radiation image. 3a of FIG. 3 is a diagram exemplarily showing the high-energy radiation image, and 3b of FIG. 3 is a diagram exemplarily showing the low-energy radiation image. A bone portion 302 in the low-energy radiation image in 3b of FIG. 3 is displayed with clear contrast compared to a bone portion 301 in the high-energy radiation image in 3a of FIG. 3.

The image processing unit 109 includes the generation unit 110, the reconstruction unit 111, and the analysis unit 112 as functional constituents. The generation unit 110 can extract a plurality of materials included in radiation images that have been captured using different radiation energies. The generation unit 110 can also generate a plurality of material characteristic images using a plurality of radiation images based on different radiation energies.

The generation unit 110 generates the material characteristic images with respect to the plurality of materials included in the radiation images that have been captured using different radiation energies. That is to say, it generates material characteristic images, such as material identification images and material separation images, from the radiation images captured by the FPD 102. The material identification images include an effective atomic number image indicating the distribution of effective atomic numbers, as well as a surface density image indicating the distribution of surface densities, with respect to a plurality of materials included in the subject. Meanwhile, the material separation images include images indicating the distribution of thicknesses or densities of respective materials when the subject is represented as two or more specific materials.

Here, effective atomic numbers denote atomic numbers corresponding to a case where chemical elements, or chemical elements of chemical compounds and mixtures, are averagely considered, and are quantification indices indicating the atomic numbers of virtual chemical elements that attenuate photons at the same rate as their component materials. The effective atomic number image refers to an image composed of an atomic number(s) corresponding to a case where the subject is represented as a single component material in units of pixels. The generation unit 110 can generate the material characteristic images, such as the effective atomic number image, from the radiation images captured by the FPD 102.

Once the control unit 105 has obtained the low-energy radiation distribution information and the high-energy radiation distribution information, which corresponds to a high energy level, from the plurality of radiation images acquired through the single radiation irradiation from the radiation generating apparatus 104 with use of the energy subtraction method, the generation unit 110 generates material characteristic images, in which a first material and a second material are separated, from the low-energy radiation distribution information and the high-energy radiation distribution information based on the result of this obtainment.

The generation unit 110 can generate images indicating the distribution of thicknesses or surface densities of a plurality of materials as the material characteristic images.

Also, the reconstruction unit 111 sets different radiation energies for respective materials, and generates a reconstructed image based on monochromatic radiation images of respective materials, which are based on different radiation energies.

For example, when the first material and the second material have been separated as the plurality of materials, the reconstruction unit 111 generates a reconstructed image based on a monochromatic radiation image based on a first radiation energy corresponding to the first material and a monochromatic radiation image based on a second radiation energy corresponding to the second material.

The reconstruction unit 111 obtains the monochromatic radiation images, in which the thicknesses or the surface densities of the materials have been multiplied by attenuation coefficients (linear attenuation coefficients or mass attenuation coefficients) corresponding to different radiation energies, and generates the reconstructed image by summing the results of multiplication performed for respective materials.

The analysis unit 112 analyzes the reconstructed image that has been generated through processing of the reconstruction unit 111, and obtains evaluation information related to contrast between the plurality of materials.

Figure 2:
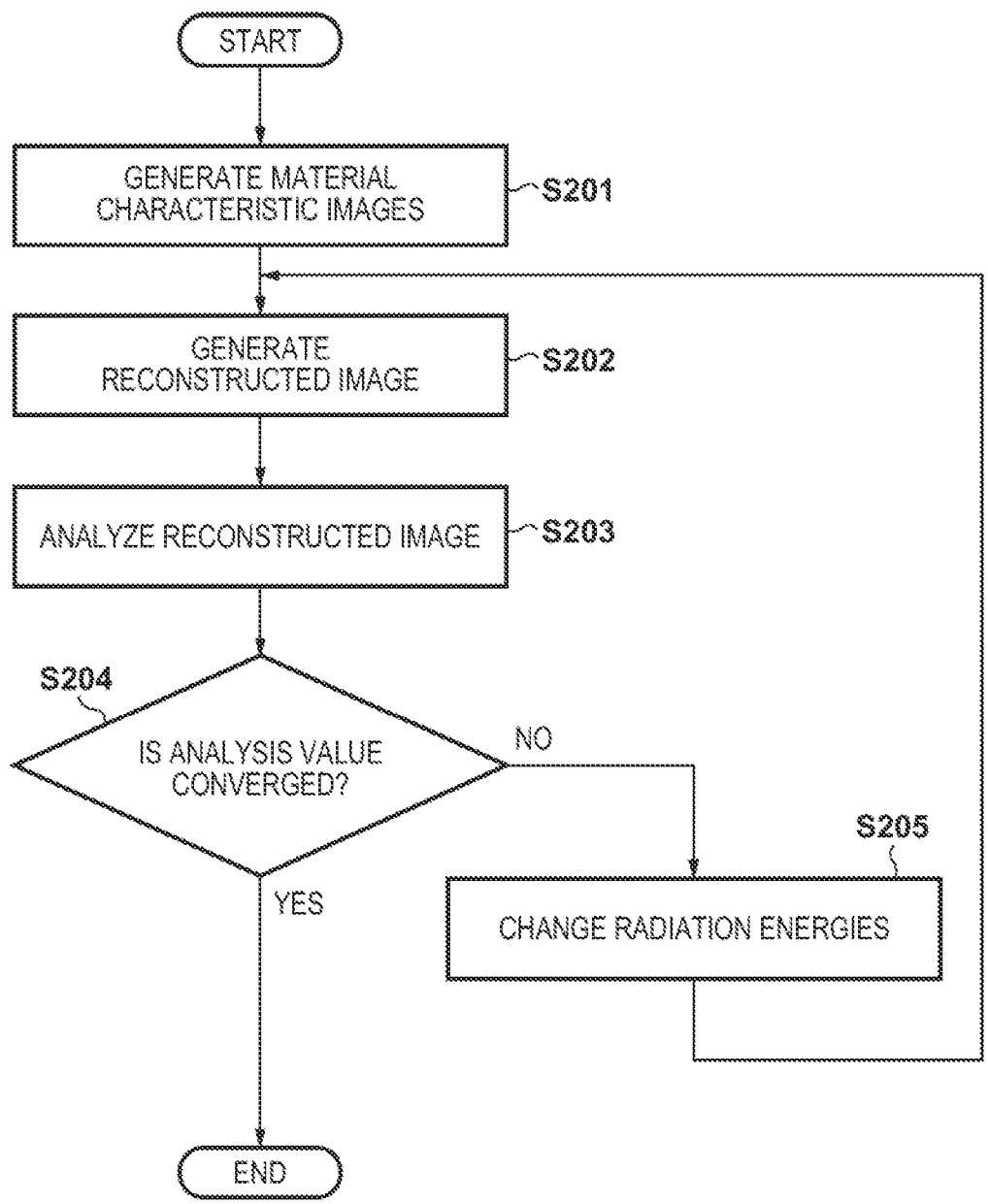
FIG. 2 is a diagram for describing a flow of processing in an image processing unit according to the first embodiment.

Next, processing in the image processing unit 109 according to the first embodiment will be described in detail using a flowchart shown in FIG. 2. The control unit 105 stores radiation images captured by the FPD 102 into the storage unit 108, and also transfers the radiation images to the image processing unit 109.

(S201: Generation of Material Characteristic Images)

In step S201, the generation unit 110 generates material separation images as material characteristic images. Specifically, the generation unit 110 generates material separation images from the high-energy radiation image shown in 3a of FIG. 3 and the low-energy radiation image shown in 3b of FIG. 3, which have been captured by the FPD 102, based on the following expressions of [Math. 1] and [Math. 2].

$$-\ln X_L = \mu_{LA} d_A + \mu_{LB} d_B \qquad [\text{Math. 1}]$$

$$-\ln X_H = \mu_{HA} d_A + \mu_{HB} d_B \qquad [\text{Math. 1}]$$

Here, $X_L$ is low-energy radiation distribution information, and the low-energy radiation distribution information ($X_L$) is an image that serves as a basis for the low-energy radiation image. On the other hand, $X_H$ is high-energy radiation distribution information, and the high-energy radiation distribution information ($X_H$) is an image that serves as a basis for the high-energy radiation image. Hereinafter, the low-energy radiation image is expressed as the low-energy radiation image $X_L$, and the high-energy radiation image is expressed as the high-energy radiation image $X_H$.

$\mu$ denotes a linear attenuation coefficient, d denotes a material thickness, indices H and L respectively denote high energy and low energy, and indices A and B respectively mean materials (e.g., body fat and bones) to be separated. Note that although body fat and bones are used here as examples of materials to be separated, no particular limitation is intended by this, and any materials can be used.

In the present embodiment, the control unit 105 functions as an obtainment unit that obtains a plurality of radiation images ($X_L$, $X_H$) that have been captured by the FPD 102 (radiation detecting apparatus) through a single radiation irradiation from the radiation source 101. The control unit 105 (obtainment unit) obtains a plurality of radiation images captured by the FPD 102 (radiation detecting apparatus) as a plurality of radiation images based on different radiation energies. The generation unit 110 generates a plurality of material characteristic images based on the plurality of radiation images ($X_L$, $X_H$) obtained by the control unit 105 (obtainment unit).

The generation unit 110 can acquire the material separation images, in which respective materials are separated, by performing computational processing for solving the simultaneous equations in the expressions of [Math. 1] and [Math. 2]. 3c of FIG. 3 is a diagram exemplarily showing a material separation image obtained based on the thickness dx of body fat, and 3d of FIG. 3 is a diagram exemplarily showing a material separation image obtained based on the thickness $d_B$ of bones.

(S202: Generation of Reconstructed Image)

In step S202, the reconstruction unit 111 generates a radiation image that has been reconstructed ($X_{proc}$) from the material separation images, which are the material characteristic images generated in step S201, based on the following expression of [Math. 3]. For example, when the separated materials are body fat and bones, the reconstruction unit 111 generates the radiation image that has been reconstructed ($X_{proc}$) from the material separation image obtained based on the thickness $d_A$ of body fat and the material separation image obtained based on the thickness $d_B$ of bones based on the following expression of [Math. 3]. Hereinafter, the radiation image that has been reconstructed ($X_{proc}$) is also referred to as a reconstructed image or a reconstructed radiation image.

$$-\ln X_{proc} = \mu_{E1A} d_A + \mu_{E2B} d_B \quad \text{[Math. 3]}$$

Here, E is single radiation energy used in the generation of the reconstructed image (Xproc), and $E_1$ and $E_2$ denote different radiation energies. d is a material thickness, and indices A and B respectively denote separated materials (body fat and bones). $\mu$ is a linear attenuation coefficient, $\mu_{E1A}$ is a linear attenuation coefficient corresponding to the radiation energy $E_{1A}$, and $\mu_{E2B}$ is a linear attenuation coefficient corresponding to the radiation energy $E_{2B}$. The reconstruction unit 111 obtains monochromatic radiation images ($\mu_{E1A}$, $\mu_{E2B} d_B$) in which the material thicknesses have been multiplied by attenuation coefficients (linear attenuation coefficients) corresponding to different radiation energies, and generates the reconstructed image ($X_{proc}$) by summing the results of multiplication performed for respective materials.

Figure 4:
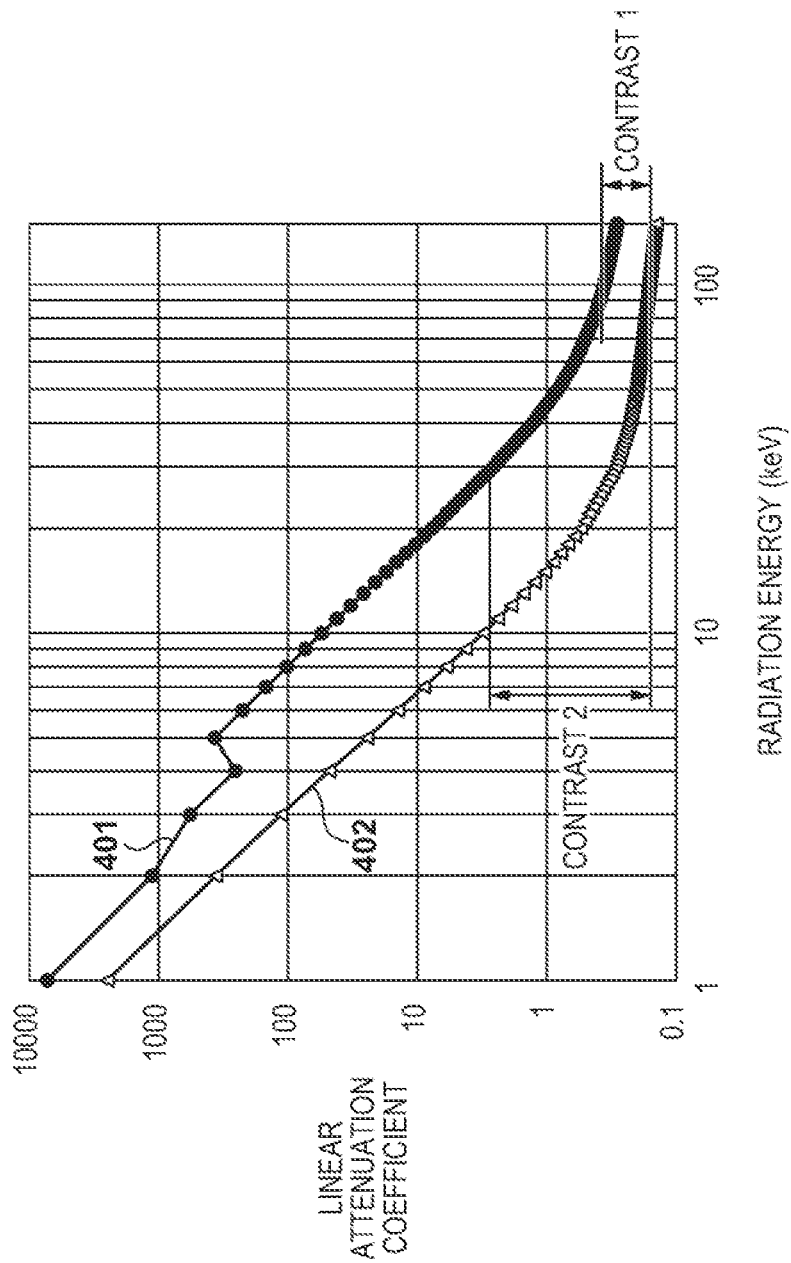
FIG. 4 is a diagram for describing the advantageous effects of the first embodiment.

FIG. 4 is a diagram for describing the advantageous effects of the first embodiment. FIG. 4 shows a correspondence relationship between radiation energy and the linear attenuation coefficient (attenuation characteristic information); a waveform 401 is a waveform indicating the attenuation characteristics for bones, and a waveform 402 is a waveform indicating the attenuation characteristics for body fat. The storage unit 108 stores the attenuation characteristic information indicating the correspondence relationship between radiation energy and the attenuation coefficient (linear attenuation coefficient, mass attenuation coefficient). The attenuation characteristic information varies with each of a plurality of materials. For example, the attenuation characteristic information varies with each of a plurality of materials as indicated by the waveforms 401, 402 of FIG. 4.

In general, when low radiation energy is transmitted through a material, image contrast increases, but noise increases as well. On the other hand, when higher radiation energy is transmitted through a material, image contrast decreases, and noise decreases as well. Relative contrast between separated images can be improved by having low radiation energy transmitted through a material (e.g., bones) for which a good view should be provided so that radiation is absorbed more and contrast is increased with respect to this material, and by having higher radiation energy transmitted through body fat portions around bones so as to reduce the influence of noise in this material, as shown in FIG. 4.

For example, when body fat and bones have been imaged (reconstructed) using a monochromatic radiation of 100 keV, relative contrast between bones and body fat is represented by contrast 1. On the other hand, when a radiation image is reconstructed by setting radiation energy on a per-material basis through processing of the present embodiment, for example, when imaging (reconstruction) is performed using monochromatic radiations based on a radiation energy of $E_1$=100 keV corresponding to body fat and a radiation energy of $E_2$=30 keV corresponding to bones, relative contrast between bones and body fat is represented by contrast 2, which is better contrast between the separated body fat and bones.

As a large part of a human body is composed of body fat, the thickness of body fat, which is a soft material, is large; if the radiation absorption is too intense, blocked-up shadows and blown-out highlights appear in a radiation image that has been reconstructed. In view of this, a radiation image is reconstructed by setting radiation energy on a per-material basis. That is to say, the reconstructed image (Xproc) is generated by setting high energy for body fat and setting low energy for bones; this makes it possible to obtain the reconstructed radiation image in which the influence of the thickness of body fat is reduced.

For example, when a value (base value) that serves as a lower limit of contrast is set, the reconstruction unit 111 can set different radiation energies for respective materials based on the attenuation characteristic information shown in FIG. 4 so that contrast between a plurality of materials exceeds the preset base value. Meanwhile, a value that serves as an upper limit of contrast is a value obtained when the analysis result has converged in a simulation that uses repetitive calculation based on the analysis on the reconstructed radiation image, which will be described later.

Note that although the reconstruction unit 111 generates the radiation image that has been reconstructed ($X_{proc}$) from the material separation images, which are the material characteristic images generated in step S201, based on the expression of [Math. 3] in the present embodiment, no limitation is intended by this example. For example, the reconstruction unit 111 can also generate the radiation image that has been reconstructed ($X_{proc}$) by extracting a plurality of materials included in radiation images that have been captured by the generation unit 110 using different radiation energies, and by using the result of applying information of the extracted materials to the expression of [Math. 3].

(S203: Analysis on Reconstructed Radiation Image)

In step S203, the analysis unit 112 analyzes the radiation image that has been reconstructed, and obtains evaluation information. The analysis unit 112 analyzes the reconstructed image (Xproc) generated in step S202. Here, information shown in the following expression of [Math. 4] can be used as the evaluation information for the analysis on the reconstructed image (Xproc). In the following expression of [Math. 4], a CNR (Contrast to Noise Ratio) obtained as a ratio between contrast between regions of interest of a plurality of materials and a standard deviation of pixel values in a region of interest of one of the plurality of materials is used as the evaluation information; however, beside this, a standard deviation SD, contrast ($M_A - M_B$) obtained as a difference between average values of pixel values in the regions of interest of the plurality of separated materials, an SN ratio (SNR: signal-to-noise ratio), and the like can also be used as the evaluation information.

$$CNR = (M_A - M_B)/SD_A \quad \text{[Math. 4]}$$

The CNR is obtained as a ratio between contrast ($M_A - M_B$) obtained as a difference between average values of pixel values in the regions of interest of the plurality of materials and a standard deviation (an SD value) of pixel values in the region of interest of one of the plurality of materials.

Here, M is an average value of pixel values in a region of interest shown in FIG. 5, and SD is a standard deviation (an SD value) of pixel values in a region of interest. An index A denotes values of a region of interest 501 of body fat, and $M_A$ denotes an average value of pixel values in the region of interest of body fat. $SD_A$ denotes a standard deviation of pixel values in the region of interest of body fat. Also, an index B denotes values of a region of interest 502 of bones, and $M_B$ denotes an average value of pixel values in the region of interest of bones. Regarding the method of setting the regions of interest, the regions of interest may be designated beforehand, or the regions of interest can also be set by an operation performed by a technician with respect to the operation unit 107 at the start of the execution of analysis processing.

(S204: Determination of Convergence of Analysis Value)

In step S204, the analysis unit 112 determines whether the CNR is the converged analysis value (optimal value). As $E_1$, $E_2$ that denote radiation energies are unknown quantities in the expression of [Math. 3] for generating the reconstructed radiation image, their initial values are set, and while making minute changes thereto, the reconstructed image (Xproc) based on an arbitrary, single radiation energy of each of the separated materials is generated using the expression of [Math. 3], and the optimal value of the CNR is acquired based on the evaluation function of the expression of [Math. 4].

As processing for determining convergence of the analysis value, the analysis unit 112 stores the evaluation information (CNR value) obtained through the first calculation into the storage unit 108. Then, the analysis unit 112 performs the convergence determination with respect to the evaluation information (CNR values) obtained through the second and subsequent repetitive calculations. The analysis unit 112 compares, for example, the evaluation information obtained through the $(n+1)^{th}$ (an integer satisfying n≥1) repetitive calculation with the evaluation information based on the $n^{th}$ calculation stored in the storage unit 108. Specifically, the evaluation information obtained through the second repetitive calculation is compared with the evaluation information based on the first calculation stored in the storage unit 108. Alternatively, the evaluation information obtained through the third repetitive calculation is compared with the evaluation information based on the second calculation stored in the storage unit 108.

For example, various types of nonlinear optimization methods, such as the bisection method, the gradient method, and the Newton's method, can be used as the optimization method. The convergence determination may be performed a set predetermined number of times, or the analysis value (optimal value) at which the radiation energy $E_1$ and the radiation energy $E_2$ converge may be obtained by calculating the evaluation information using all combinations of the radiation energies $E_1$, $E_2$ while changing the radiation energies $E_1$, $E_2$ at an interval of a minute change amount $\Delta E$ of the radiation energies. For example, in the case of a general radiation device, as the radiation energies $E_1$, $E_2$ can take a range of approximately 20 keV to 200 keV, the radiation energies $E_1$, $E_2$ can be changed in this range as a preset range. Furthermore, as the reconstructed image (Xproc) can also be generated in other ranges, the analysis value (optimal value) at which the radiation energy $E_1$ and the radiation energy $E_2$ converge may be obtained by changing the preset range and by changing the radiation energies $E_1$, $E_2$ in the changed range.

Alternatively, a time point at which the evaluation information (CNR value) of the expression of [Math. 4] ceased to fluctuate in the repetitive calculations may be set. For example, the analysis unit 112 can determine that the evaluation information has converged when the difference in the evaluation information or the rate of change in the evaluation information, which is obtained from the comparison result, is equal to or below a base value of the convergence determination.

When the evaluation information (CNR value) has converged in the convergence determination of step S204 (S204—Yes), processing is ended. On the other hand, when the evaluation information has not converged in the convergence determination of step S204 (S204—No), the analysis unit 112 causes processing to proceed to step S205.

(S205: Changing of Radiation Energies $E_1$, $E_2$)

When it is determined that the convergence of the analysis value is not sufficient in step S204, the analysis unit 112 changes the radiation energies $E_1$, $E_2$ in step S205. The analysis unit 112 sets different radiation energies for respective materials so that the evaluation information has the maximum value. For example, in order to increase the difference between the two radiation energies $E_1$, $E_2$ one radiation energy (e.g., $E_1$) may be fixed while changing the other radiation energy (e.g., $E_2$) to larger monochromatic radiation energy. After the radiation energies have been changed, the analysis unit 112 causes processing to return to step S202.

In step S202, the reconstruction unit 111 generates the reconstructed image ($X_{proc}$) based on different radiation energies whose settings have been changed. That is to say, the reconstruction unit 111 obtains linear attenuation coefficients μ corresponding to the changed radiation energies $E_1$, $E_2$, and generates the reconstructed image (Xproc) based on the expression of [Math. 3]. Then, in step S203, the analysis unit 112 analyzes the evaluation information based on the generated reconstructed image (Xproc), and processing of step 202 to step 205 is repeated until the convergence is determined to be sufficient in step S204.

The analysis unit 112 determines whether the evaluation information obtained through the repetitive calculations has converged, and when the evaluation information has converged, the reconstruction unit 111 sets the radiation energies used in calculating the evaluation information that has converged as different radiation energies for respective materials. When the result of analysis on the evaluation information has converged and different radiation energies $E_1$, $E_2$ have been finally set for respective separated materials, the reconstruction unit 111 obtains linear attenuation cofficients μ corresponding to the set radiation energies $E_1$, $E_2$ based on the attenuation characteristic information stored in the storage unit 108, generates the reconstructed image (Xproc) using the expression of [Math. 3], and outputs the reconstructed image (Xproc) to the monitor 106 (display unit).

The monitor 106 (display unit) can display radiation images (digital images) that the control unit 105 has received from the FPD 102, and images that have undergone image processing in the image processing unit 109. The display control unit 116 causes the monitor 106 (display unit) to display the reconstructed image (Xproc) generated by the reconstruction unit 111. Furthermore, the display control unit 116 can also perform display control so as to cause the monitor 106 (display unit) to display the reconstructed image (Xproc) and the material separation images, which are the material characteristic images, in an aligned manner. Moreover, the display control unit 116 can also perform display control so that at least one image that has been selected by the technician from among images displayed on the monitor 106 (display unit) is displayed by the display unit.

According to the present embodiment, even in general imaging and fluoroscopic imaging, a radiation image can be reconstructed by setting radiation energy for each of a plurality of materials without using tomographic images, and an image in which a specific material is enhanced can readily be obtained.

Second Embodiment

While the first embodiment has been described in relation to a configuration that acquires radiation energies through analysis, the present embodiment will be described in relation to a configuration that shortens an analysis period for determining radiation energies $E_1$, $E_2$ corresponding to separated materials by holding beforehand the values of the radiation energies $E_1$, $E_2$ in a table and the like.

Below, the description of parts that are similar to the first embodiment will be omitted to avoid duplication, and only the constituent parts that are unique to a second embodiment will be described. The configuration of the present embodiment has advantageous effects that are beneficial when real-time effects are required, such as during fluoroscopic imaging.

FIG. 7 is a diagram exemplarily showing a structure of a table that holds the values of radiation energies $E_1$, $E_2$, and the storage unit 108 holds the table in which information of a subject is associated with different radiation energies for respective materials. The information of the subject includes information of the body thicknesses of the subject or information of the thicknesses of materials. The table shown in FIG. 7 holds the values of radiation energies in correspondence with the thicknesses of the subject as the information of the subject. Once the body thickness of the subject can be acquired, different radiation energies $E_1$, $E_2$ corresponding to the thickness of the subject can be obtained.

Processing in the image processing unit 109 according to the second embodiment will be described in detail using a flowchart shown in FIG. 6. First, in step S601, the generation unit 110 generates material separation images, which are material characteristic images. This processing is processing that is similar to processing of step S201 of the flowchart that has been described using FIG. 2.

In step S602, with reference to the table stored in the storage unit 108, the reconstruction unit 111 sets different radiation energies $E_1$, $E_2$ for respective materials, which correspond to the information of the subject to be imaged. Regarding the body thickness of the subject, the body thickness of the subject may be obtained based on imaging information, the body thickness of the subject may be selected by a technician via the operation unit 107, or the body thickness of the subject may be estimated from the thicknesses of respective materials (e.g., the thickness of body fat) in the material separation images.

In step S603, the reconstruction unit 111 generates a reconstructed image (Xproc) from the material separation images (images of the thicknesses of body fat and bones), which are the material characteristic images generated in step S601, based on the expression of [Math. 3]. Here, single radiation energy E: and single radiation energy $E_2$ used in the generation of the reconstructed image (Xproc) are values that have been set in step S602 with reference to the table.

The display control unit 116 causes the monitor 106 (display unit) to display the reconstructed image (Xproc) generated by the reconstruction unit 111. The display control unit 116 causes the monitor 106 (display unit) to display, together with the displayed reconstructed image (Xproc), a scroll bar as a user interface (UI) for continuously changing the settings of different radiation energies $E_1$, $E_2$. The radiation energies $E_1$, $E_2$ can be continuously changed as the technician operates the scroll bar. The reconstruction unit 111 can generate the reconstructed image (Xproc) by obtaining attenuation characteristic information corresponding to the radiation energies $E_1$, $E_2$ that have been changed by the operation performed on the user interface (scroll bar) with reference to FIG. 4. The display control unit 116 causes the monitor 106 (display unit) to display the reconstructed image (Xproc) generated based on the changed radiation energies.

While continuously changing the values of the radiation energies $E_1$, $E_2$, the technician can observe changes in the reconstructed image (Xproc) that is generated in correspondence with the change. For example, if a lesion is enhanced when the attenuation for components of bones is increased (when low radiation energy is set), it will be found that the lesion is related to bones. This makes it possible to distinguish whether the lesion is a lesion dependent on components of body fat or a lesion dependent on components of bones.

Furthermore, in step S602, the display control unit 116 can also cause the monitor 106 (display unit) to display values held in the table as recommended values. With reference to the values displayed on the monitor 106 (display unit), the technician can change the values of radiation energies via the operation unit 107 so as to enhance the material that he/she wants to view. The reconstruction unit 111 generates the reconstructed image (Xproc) by obtaining, from FIG. 4, linear attenuation coefficients corresponding to the radiation energies $E_1$, $E_2$ that have been changed in accordance with an input from the operation unit 107, and the display control unit 116 causes the monitor 106 (display unit) to display the reconstructed image (Xproc) generated based on the changed radiation energies.

According to the present embodiment, as the values of radiation energies $E_1$, $E_2$ are held in the table beforehand, a favorable reconstructed radiation image can be generated without executing processing of the optimization method. In fluoroscopic imaging, for example, a rendering speed of approximately 15 FPS is demanded; thus, processing of the present embodiment can also be applied to processing during, for example, fluoroscopic imaging in which real-time effects are required.

According to the present embodiment, even in general imaging and fluoroscopic imaging, a radiation image can be reconstructed by setting radiation energy for each of a plurality of materials without using tomographic images, and an image in which a specific material is enhanced can readily be obtained.

Third Embodiment

A third embodiment will be described in relation to a configuration that acquires the values of radiation energies $E_1$, $E_7$ corresponding to effective atomic numbers $Z_1$, $Z_2$ through analysis. A configuration example of the radiation imaging system 100 according to the third embodiment of the present invention is similar to that of the radiation imaging system 100 of FIG. 1 described in the first embodiment, and the radiation imaging system 100 includes the radiation generating apparatus 104, the radiation source 101, the FPD 102 (radiation detecting apparatus), and the information processing apparatus 120. The description of parts that overlap the configuration of the first embodiment will be omitted, and different parts will be described.

Once the control unit 105 has obtained low-energy radiation distribution information and high-energy radiation distribution information, which corresponds to a high energy level, from a plurality of radiation images acquired through a single radiation irradiation from the radiation generating apparatus 104 with use of the energy subtraction method, the generation unit 110 generates material characteristic images with respect to a plurality of materials included in the radiation images based on the result of this obtainment. The generation unit 110 generates images in which the plurality of materials are separated (material separation images) as material characteristic images from the low-energy radiation distribution information and the high-energy radiation distribution information. The generation unit 110 can generate images indicating the distribution of the thicknesses or densities of the plurality of materials as the separated images (material separation images).

Also, the generation unit 110 generates images indicating the distribution of the plurality of materials (material identification images) as material characteristic images from the low-energy radiation distribution information and the high-energy radiation distribution information. The generation unit 110 can generate an image indicating the distribution of effective atomic numbers of the plurality of materials, or a surface density image indicating the distribution of surface densities of the materials, as the images indicating the distribution of the plurality of materials (material identification images).

Furthermore, the reconstruction unit 111 sets different radiation energies (monochromatic radiation energies) for respective positions of the plurality of materials, and generates a reconstructed image based on different radiation energies. Here, a position of a material includes a pixel, or a region composed of a plurality of pixels, in a radiation image. That is to say, the reconstruction unit 111 can set different radiation energies for respective pixels as the positions of the materials. Alternatively, the reconstruction unit 111 can set different radiation energies for respective regions composed of a plurality of pixels as the positions of the materials.

As specific processing, the reconstruction unit 111 generates, as a reconstructed image, a monochromatic radiation image in which attenuation coefficients (mass attenuation coefficients) corresponding to different radiation energies for respective positions of the plurality of materials by the surface densities of respective pixels. Here, the attenuation coefficients (mass attenuation coefficients) are information associated with information of the plurality of materials and radiation energies, and the information of the plurality of materials includes the effective atomic numbers of the materials or information of the plurality of materials that have been separated (e.g., the thicknesses of the materials).

The analysis unit 112 generates an energy table in which the plurality of materials are associated with different radiation energies. The analysis unit 112 generates the energy table in which single radiation energy is associated with the effective atomic number $Z_{\mathit{eff}\_i}$ at each pixel as radiation energy (reconstruction energy) used in the generation of the reconstructed image. With reference to the energy table, the reconstruction unit 111 sets different radiation energies for respective positions of the plurality of materials.

Next, processing in the image processing unit 109 according to the third embodiment will be described in detail using a flowchart shown in FIG. 8. The control unit 105 stores radiation images captured by the FPD 102 into the storage unit 108, and also transfers the radiation images to the image processing unit 109.

(S801: Generation of Material Characteristic Images)

In step S801, the generation unit 110 generates material separation images or material identification images as material characteristic images. Specifically, the generation unit 110 generates the material separation images from the high-energy radiation image shown in 3a of FIG. 3 and the low-energy radiation image shown in 3b of FIG. 3, which have been captured by the FPD 102, based on the expressions of [Math. 1] and [Math. 2] described in the first embodiment.

In the present embodiment, the generation unit 110 obtains a logarithmic ratio ($\ln X_L / \ln X_H$) between the low-energy radiation distribution information ($X_L$) and the high-energy radiation distribution information ($X_H$), and generates an effective atomic number image $Z_{\mathit{eff}}$ based on the obtained logarithmic ratio. FIG. 9 is a diagram showing a relationship between the logarithmic ratio between the low-energy and high-energy radiation distribution information pieces and the effective atomic number Z; the relationship between the logarithmic ratio and the effective atomic number Z shown in FIG. 9 is formed as a table and stored into the storage unit 108 in advance. With reference to the table, the generation unit 110 can generate the effective atomic number image $Z_{\mathit{eff}}$ by identifying the effective atomic number Z corresponding to the logarithmic ratio for each pixel (pixel position, or region composed of a plurality of pixels). Based on the effective atomic number image $Z_{\mathit{eff}}$, the generation unit 110 can generate a surface density image D indicating the distribution of the surface densities of materials corresponding to the effective atomic numbers.

FIG. 10 is a diagram exemplarily showing the effective atomic numbers of materials. For example, the effective atomic number of body fat is 5.9 to 6.5, and the effective atomic number of water is 7.4. Also, the effective atomic number of muscles is 7.4 to 7.6, and the effective atomic number of bones is 12.3 to 13.8. In this way, specific regions that compose a human body (subject), such as body fat, water, muscles, and bones, can be identified with the effective atomic numbers.

The effective atomic number of iodine included in a contrast agent and the like is 53, the effective atomic number of barium is 56, and the effective atomic number of stainless as a member used for a guide wire of a catheter and the like is 26. Also, the effective atomic number of titanium as a member used for a stent is 22. With use of information of the effective atomic numbers, materials that exist inside a human body (subject) can be identified in accordance with an imaging technique.

Note that the generation unit 110 can also obtain the effective atomic number image Z and the surface density image D by solving simultaneous equations based on the mass attenuation coefficients, the low-energy radiation distribution information ($X_L$), and the high-energy radiation distribution information ($X_H$), instead of using the expressions of [Math. 1] and [Math. 2] described in the first embodiment.

(S802: Generation of Energy Table)

In step S802, the analysis unit 112 generates the energy table in which the plurality of materials are associated with different radiation energies.

Figure 11:
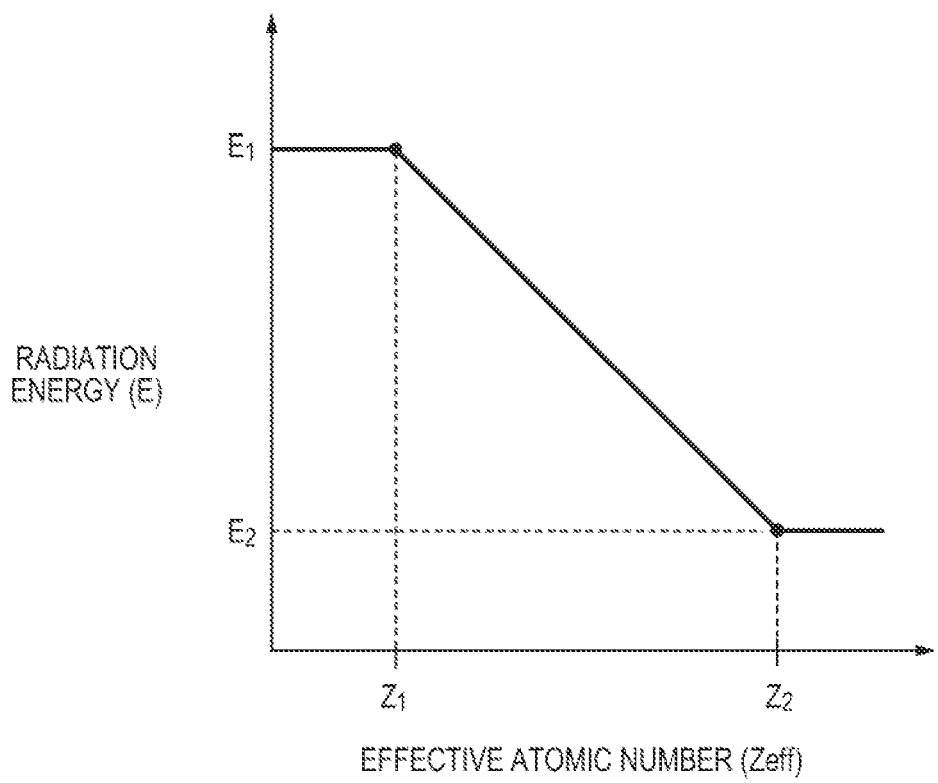
FIG. 11 is a diagram exemplarily showing an energy table in which the effective atomic numbers are each associated with single radiation energy.

FIG. 11 is a diagram exemplarily showing the energy table in which the effective atomic numbers are each associated with single radiation energy. In FIG. 11, a vertical axis represents radiation energy (E), and a horizontal axis represents an effective atomic number ($Z_{\mathit{eff}}$). Based on histogram analysis, effective atomic numbers $Z_1$, $Z_2$ can respectively be an effective atomic number corresponding to a first percent from the bottom (e.g., 5% from the bottom), and an effective atomic number corresponding to a second percent from the top (e.g., 5% from the top), of the effective atomic numbers in the effective atomic number image.

Figure 12:
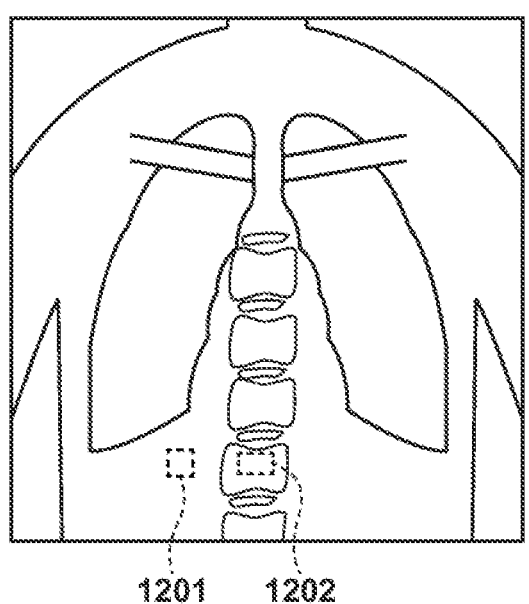
FIG. 12 is a diagram exemplarily showing regions of interest in a radiation image.

FIG. 12 is a diagram exemplarily showing regions of interest in a radiation image. As shown in FIG. 12, it is permissible to perform location recognition by executing image processing with respect to the radiation image, extract a first material (e.g., body fat), a second material (e.g., bones), and a third material (e.g., a medical device, such as a catheter and a stent), and use the values of corresponding effective atomic numbers of the materials as effective atomic numbers in the energy table. For example, an average value of the effective atomic numbers in a region of interest 1201 of the first material (e.g., body fat) may be used as $Z_1$, and an average value of the effective atomic numbers in a region of interest 1202 of the second material (e.g., bones) may be used as $Z_2$.

Figure 13A:
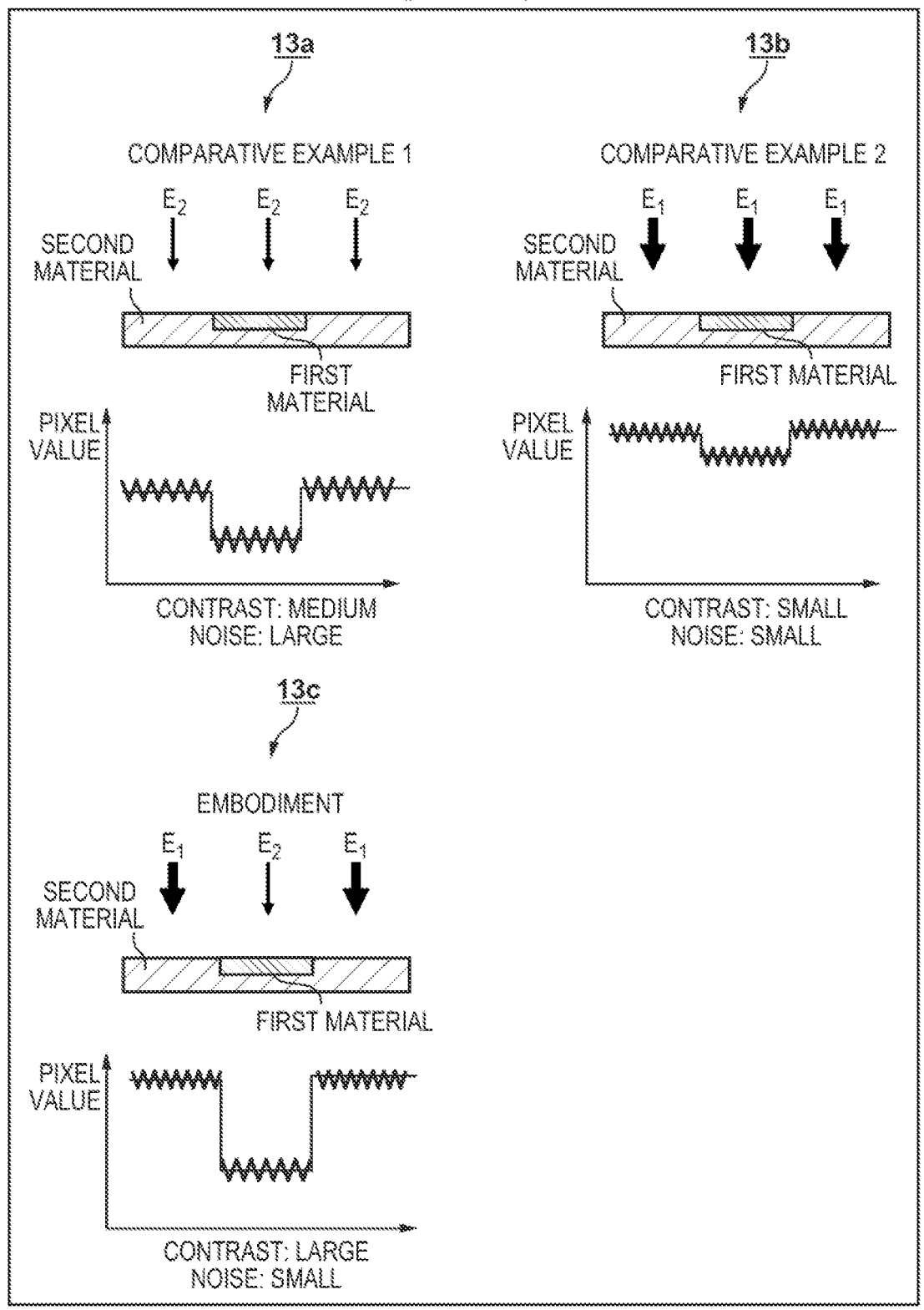
FIG. 13A is a diagram schematically showing a relationship between radiation energy and noise.

Radiation energies to be associated with the effective atomic numbers $Z_1$, $Z_2$ may be acquired by performing optimization using average values of the effective atomic numbers of pixels corresponding to the plurality of materials or the effective atomic numbers in the regions of interest 1201, 1202 corresponding to the plurality of materials. FIG. 13A is a diagram schematically showing a relationship between radiation energy and noise; in FIGS. 13A, 13a and 13b are diagrams showing a first comparative example and a second comparative example, and 13c is a diagram showing processing of the present embodiment.

As shown in 13a (the first comparative example) of FIG. 13A, in general, when low radiation energy $E_2$ is transmitted through the first material and the second material, overall contrast between images of the first material and the second material increases, but overall noise increases as well. On the other hand, as shown in 13b (the second comparative example), when higher radiation energy $E_1$ is transmitted through the images of the first material and the second material, contrast between the images of the first material and the second material decreases, and noise decreases as well. As shown in 13a, 13b of FIG. 13A, the ratio of noise to contrast between the images (CNR) is substantially constant.

In the present embodiment, as shown in 13c of FIG. 13A, different radiation energies are set for respective pixels of different materials, or respective regions of different materials, by having low radiation energy $E_2$ transmitted through the first material (e.g., bones) for which a good view should be provided so that radiation is absorbed more and contrast is increased with respect to this material, and by having higher radiation energy $E_1$ transmitted through the second material (e.g., body fat) around bones so as to reduce the influence of noise in this material: in this way, the ratio of noise to relative contrast between the image of the first material and the image of the second material (CNR) is improved.

As radiation energies corresponding to effective atomic numbers are unknown quantities in the following expression of [Math. 5] for generating a reconstructed radiation image, the initial values of respective radiation energies are set, and while making changes to the radiation energies at an interval of a minute change amount $\Delta E$ of the radiation energies, the reconstruction unit 111 sequentially generates reconstructed images ($X_{proc}$) based on different radiation energies whose settings have been gradually changed with use of the expression of [Math. 5]; the analysis unit 112 analyzes the reconstructed images ($X_{proc}$) and obtains evaluation information related to contrast between the plurality of materials.

The evaluation information includes contrast obtained as a difference between average values of pixel values in respective regions corresponding to the plurality of materials. Furthermore, the evaluation information includes a CNR (Contrast to Noise Ratio) obtained as a ratio between contrast between regions corresponding to the plurality of materials and a standard deviation of pixel values in a region corresponding to one of the plurality of materials. Moreover, a standard deviation SD, an SN ratio (SNR: signal-to-noise ratio), and the like can also be used as the evaluation information. The analysis unit 112 sets different radiation energies ($E_1$, $E_2$) for respective materials so that the evaluation information has the maximum value.

In generating the energy table shown in FIG. 11, the settings of the effective atomic numbers $Z_1$, $Z_2$ can also be set in advance based on known information. For example, as the effective atomic number of body fat and the effective atomic number of bones are known, these effective atomic numbers may be preset.

Furthermore, in generating the energy table shown in FIG. 11, while linear interpolation is performed between the radiation energy $E_1$ (the effective atomic number $Z_1$) and the radiation energy $E_2$ (the effective atomic number $Z_2$), interpolation may be performed using logarithmic interpolation and a sigmoid function. Moreover, while the values equal to or smaller than the effective atomic number $Z_1$ and the values equal to or larger than the effective atomic number $Z_2$ are fixed values in order to prevent artifact in FIG. 11, they may be extrapolated through linear interpolation and the like.

In the case of a general radiation imaging apparatus, the radiation energies $E_1$, $E_2$ to be associated with the effective atomic numbers $Z_1$, $Z_2$ are approximately 20 keV to 200 keV; thus, the radiation energies $E_1$, $E_2$ can be set in this range as a preset range. Furthermore, the radiation energies $E_1$, $E_2$ can also be set in other ranges. Although the effective atomic number image is used as an example in the present description, similar processing can be performed also by associating information (thickness or density) of each material after the material separation, which has been obtained based on the expressions of [Math. 1] and [Math. 2] described in the first embodiment, with single radiation energy during the reconstruction. In this case, it is sufficient for the analysis unit 112 to set the information (thickness or density) of each material after the energy/material separation on the horizontal axis of the energy table, and set single radiation energy to be associated with the information of each material on the vertical axis of the energy table.

(S803: Generation of Reconstructed Image)

In step S803, with reference to the energy table, the reconstruction unit Ill sets different radiation energies (monochromatic radiation energies) for respective positions of the plurality of materials, and generates a reconstructed image based on different radiation energies. The reconstruction unit 111 generates a radiation image that has been reconstructed ($X_{proc}$) from the effective atomic number image ($Z_{eff}$) and the surface density image (D) generated in step S801 based on the following expression of [Math. 5]. Hereinafter, the radiation image that has been reconstructed ($X_{proc}$) is also referred to as a reconstructed image or a reconstructed radiation image.

$$-\ln X_{proc_i} = \mu_i(E_i, Z_{eff_i}) \times D_i \qquad \text{[Math. 5]}$$

Here, E is single radiation energy used in the generation of the reconstructed image ($X_{proc}$), and an index i denotes a pixel. $D_i$ denotes the surface density of each pixel. $\mu_i$ is a mass attenuation coefficient, and the mass attenuation coefficient $\mu_i$ corresponds to the effective atomic number $Z_{eff\,i}$ and the radiation energy $E_i$ at each pixel. A correspondence relationship between the effective atomic number and the radiation energy at each pixel is determined by, for example, the energy table of FIG. 11; once the effective atomic numbers at respective pixels can be identified based on the effective atomic number image ($Z_{eff}$), the corresponding radiation energies can be set for respective pixel positions or respective regions composed of a plurality of pixels.

The storage unit 108 stores a table that holds information of attenuation coefficients corresponding to the effective atomic numbers of and the radiation energies for the materials (mass attenuation coefficients $\mu$ (Z, E)). Creating the table of the mass attenuation coefficients $\mu$ (Z, E) corresponding to the effective atomic numbers Z and the radiation energies E and storing the table into the storage unit 108 enables the reconstruction unit 111 to obtain the mass attenuation coefficients $\mu$ (Z, E) with reference to the table.

Based on the expression of [Math. 5], the reconstruction unit 111 generates the reconstructed image ($X_{proc}$) based on attenuation coefficient information related to the attenuation coefficients corresponding to the effective atomic numbers of and the radiation energies for the materials (mass attenuation coefficients $\mu$ (Z, E)), and on the surface density image D indicating the distribution of the surface densities of the plurality of materials.

FIG. 13B is a diagram for describing the advantageous effects of the third embodiment. FIG. 13B shows a correspondence relationship between radiation energies and mass attenuation coefficients (attenuation characteristic information); a waveform 1301 is a waveform indicating the attenuation characteristics of the first material (e.g., bones), and a waveform 1302 is a waveform indicating the attenuation characteristics of the second material (e.g., body fat). As indicated by the waveforms 1301, 1302 of FIG. 13B, the attenuation characteristic information varies with each of the plurality of materials (effective atomic numbers).

For example, when body fat and bones have been imaged (reconstructed) using a monochromatic radiation of 100 keV, relative contrast between body fat and bones is represented by contrast 1. On the other hand, when the radiation image is reconstructed by setting radiation energy for each material position (pixel or region), for example, when imaging (reconstruction) is performed using monochromatic radiations based on a radiation energy of 100 keV corresponding to pixels of the second material (e.g., body fat) and a radiation energy of 30 keV corresponding to pixels of the first material (e.g., bones), relative contrast between the pixels of bones and the pixels of body fat is represented by contrast 2, which is better contrast between the pixels of body fat and the pixels of bones.

As a large part of a human body is composed of body fat, the thickness of body fat, which is a soft material, is large; if the radiation absorption is too intense, blocked-up shadows and blown-out highlights appear in a radiation image that has been reconstructed. In view of this, a radiation image is reconstructed by setting radiation energies for respective pixels (pixel positions or regions composed of a plurality of pixels) based on the effective atomic numbers of respective materials. For example, the reconstructed image ($X_{proc}$) is generated by setting high energy for pixels indicating the effective atomic number of the second material (e.g., body fat), and by setting low energy for pixels indicating the effective atomic number of the first material (e.g., bones); this makes it possible to obtain the reconstructed radiation image in which the first material is enhanced and the influence of the second material is reduced.

The monitor 106 (display unit) can display radiation images (digital images) that the control unit 105 has received from the FPD 102, and images that have undergone image processing in the image processing unit 109. The display control unit 116 causes the monitor 106 (display unit) to display the reconstructed image (Xproc) generated by the reconstruction unit 111.

According to the present embodiment, even in general imaging and fluoroscopic imaging, a radiation image can be reconstructed by setting different radiation energies for respective positions of a plurality of materials without using tomographic images, and an image in which a specific material is enhanced can readily be obtained.

Note that although the reconstruction unit 111 generates the radiation image that has been reconstructed ($X_{proc}$) from the effective atomic number image ($Z_{eff}$) and the surface density image (D), which have been generated in step S801, based on the expression of [Math. 5] in the present embodiment, no limitation is intended by this example. For example, the reconstruction unit ill can also generate the radiation image that has been reconstructed ($X_{proc}$) by extracting a plurality of materials included in radiation images that have been captured by the generation unit 110 using different radiation energies, and by using the result of applying information of the extracted materials to the expression of [Math. 5].

Fourth Embodiment

While the third embodiment has been described in relation to a configuration that acquires the values of radiation energies $E_1$, $E_2$ corresponding to the effective atomic numbers $Z_1$, $Z_2$ through analysis, the present embodiment will be described in relation to a configuration in which the storage unit 108 holds, beforehand, an energy table in which the values of radiation energies $E_1$, $E_2$ have been set by an operation performed by a technician on the operation unit 107.

The present embodiment will be described in relation to a configuration that, in generating the energy table of FIG. 11, obtains the values of radiation energies $E_1$, $E_2$ from the storage unit 108, and generates the energy table of FIG. 11 based on the obtained radiation energies $E_1$, $E_2$.

Below, the description of parts that are similar to the third embodiment will be omitted to avoid duplication, and only the constituent parts that are unique to the fourth embodiment will be described. The configuration of the present embodiment has advantageous effects that are beneficial when a reconstructed image is generated based on an energy spectral that the technician wants to enhance during capturing of a still image, rather than when real-time effects are required during fluoroscopic imaging.

Processing in the image processing unit 109 according to the fourth embodiment will be described in detail using a flowchart of FIG. 8. First, in step S801, the generation unit 110 generates material identification images, which are material characteristic images. Here, the material identification images include an effective atomic number image indicating the distribution of effective atomic numbers, as well as a surface density image indicating the distribution of surface densities, with respect to a plurality of materials included in a subject.

In step S802, the analysis unit 112 obtains the set radiation energies $E_1$, $E_2$ with reference to the table stored in the storage unit 108. The values of the radiation energies $E_1$, $E_2$ can be arbitrarily set by the technician via the operation unit 107; for example, a plurality of types of tables that hold the radiation energies $E_1$, $E_2$ in accordance with imaging information, such as locations of subjects to be imaged and body types of subjects, can be stored into the storage unit 108.

The analysis unit 112 generates the energy table based on the radiation energies $E_1$, $E_2$ that have been set via the operation unit 107. The analysis unit 112 can also generate the energy table based on radiation energies which are included among the plurality of radiation energies that have been preset via the operation unit 107 and which have been changed in accordance with the imaging information. For example, based on the radiation energies $E_1$, $E_2$ obtained with reference to the table that has been changed in accordance with imaging conditions and the like, the analysis unit 112 generates the energy table in which the effective atomic numbers $Z_1$, $Z_2$ are associated with the radiation energies $E_1$, $E_2$ (FIG. 11).

In step S803, the reconstruction unit 111 generates a reconstructed image ($X_{proc}$) from the effective atomic number image ($Z_{eff}$) and the surface density image (D), which are the material identification images generated in step S801, based on the expression of [Math. 3]. In generating the reconstructed image ($X_{proc}$), the reconstruction unit 111 refers to the energy table (FIG. 11) generated in step S802, and generates the reconstructed image ($X_{proc}$) based on the effective atomic number $Z_{eff\ i}$ at each pixel and the mass attenuation coefficient $\mu_i$ corresponding to the radiation energy $E_i$.

Once the effective atomic numbers at respective pixels can be identified based on the effective atomic number image ($Z_{eff}$), the corresponding radiation energies can be set for respective pixel positions or respective regions composed of a plurality of pixels.

Once the effective atomic number Z and the radiation energy E have been determined, the mass attenuation coefficient $\mu$ (Z, E) corresponding to the effective atomic number Z and the radiation energy E can be obtained with reference to the table in the storage unit 108.

Based on the expression of [Math. 3], the reconstruction unit 111 generates the reconstructed image ($X_{proc}$) based on attenuation coefficient information related to the attenuation coefficients corresponding to the effective atomic numbers of and the radiation energies for the materials (mass attenuation coefficients $\mu$ (Z, E)), and on the surface density image D indicating the distribution of the surface densities of the plurality of materials.

The display control unit 116 causes the monitor 106 (display unit) to display the reconstructed image ($X_{proc}$) generated by the reconstruction unit 111. The display control unit 116 causes the monitor 106 (display unit) to display, together with the displayed reconstructed image ($X_{proc}$), a scroll bar as a user interface (U) for continuously changing the settings of different radiation energies $E_1$, $E_2$.

The radiation energies $E_1$, $E_2$ can be continuously changed as the technician operates the scroll bar. Based on the radiation energies $E_1$, $E_2$ that have been changed by operating the user interface (scroll bar), the analysis unit 112 generates the energy table in which the different effective atomic numbers $Z_1$, $Z_2$ are associated with the radiation energies $E_1$, $E_2$ (FIG. 11).

The reconstruction unit 111 can obtain the mass attenuation coefficients $\mu$ (Z, E) with reference to the energy table that has been generated based on the changed radiation energies $E_1$, $E_2$, and the reconstruction unit 111 can generate the reconstructed image ($X_{proc}$) based on the obtained mass attenuation coefficients $\mu$ (Z, E) and on the surface density image D indicating the distribution of the surface densities of the plurality of materials.

While continuously changing the values of the radiation energies $E_1$, $E_2$, the technician can observe changes in the reconstructed image ($X_{proc}$) that is generated in correspondence with the change. For example, if a lesion is enhanced when the attenuation for components of bones is increased (when low radiation energy is set), it will be found that the lesion is related to bones. This makes it possible to distinguish whether the lesion is a lesion dependent on components of body fat or a lesion dependent on components of bones.

According to the present embodiment, as the values of radiation energies $E_1$, $E_2$ are held in the table beforehand, a favorable reconstructed radiation image can be generated without executing processing of the optimization method. For example, the reconstructed radiation image can be generated based on an energy spectrum that the technician wants to enhance during capturing of a still image.

According to the present embodiment, even in general imaging and fluoroscopic imaging, a radiation image can be reconstructed by setting different radiation energies for respective positions of a plurality of materials without using tomographic images, and an image in which a specific material is enhanced can readily be obtained.

According to the present embodiment, a radiation image can be reconstructed by setting different radiation energies for respective materials.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

The invention claimed is:

1. A radiation imaging apparatus, comprising at least one of (a) one or more processors connected to one or more memories storing a program including instructions executed by the one or more processors and (b) circuitry configured to function as:

a generating unit configured to generate monochromatic radiation images of different radiation energies for materials using material characteristic images of the materials generated by performing energy subtraction using radiation distribution information pieces corresponding to different radiation energies;

a reconstructing unit configured to generate a reconstructed image by compositing the monochromatic radiation images; and an analyzing unit configured to analyze the reconstructed image to obtain evaluation information by comparing information related to pixel values in regions of interest of the materials, wherein the reconstructing unit generates a new reconstructed image by compositing new monochromatic radiation images of different radiation energies changed using the evaluation information.

2. A radiation imaging apparatus, comprising at least one of (a) one or more processors connected to one or more memories storing a program including instructions executed by the one or more processors and (b) circuitry configured to function as:

an obtaining unit configured to obtain first energy radiation distribution information and second energy radiation distribution information that corresponds to a first energy level and a second energy level from radiation images obtained through a single radiation irradiation from a radiation generating unit;

a generating unit configured to generate (i) a first monochromatic radiation image of first radiation energy for a first material and (ii) a second monochromatic radiation image of second radiation energy for a second material, using material characteristic images of the first material and the second material generated by performing energy subtraction using the first radiation distribution information and the second energy radiation distribution information;

a reconstructing unit configured to generate a reconstructed image by compositing the first monochromatic radiation image and the second monochromatic radiation image; and an analyzing unit configured to analyze the reconstructed image to obtain evaluation information by comparing information related to pixel values in regions of interest of the first material and the second material, wherein the reconstructing unit generates a new reconstructed image by compositing a new first monochromatic radiation image and a new second monochromatic radiation image of first radiation energy and second radiation energy, changed using the evaluation information.

3. The radiation imaging apparatus according to claim 1, further comprising a generating unit configured to generate material characteristic images of the materials using the different radiation energies, wherein the generating unit generates images indicating a distribution of thicknesses or surface densities of the materials as the material characteristic images.

4. The radiation imaging apparatus according to claim 3, wherein the reconstructing unit is configured to obtain monochromatic radiation images in which the thicknesses or the surface densities of the materials have been multiplied by attenuation coefficients corresponding to the different radiation energies, and to generate the reconstructed image by summing results of multiplication performed for the respective materials.

5. The radiation imaging apparatus according to claim 1, further comprising a generating unit configured to generate material characteristic images of the materials using the different radiation energies, wherein the generating unit generates the material characteristic images of the materials based on a result of performing energy subtraction.

6. The radiation imaging apparatus according to claim 1, wherein at least one of (a) the one or more processors connected to the one or more memories storing a program including instructions executed by the one or more processors and (b) the circuitry configured to function as a storing unit configured to store attenuation characteristic information indicating a correspondence relationship between radiation energy and an attenuation coefficient, the attenuation characteristic information varying with each of the plurality of materials.

7. The radiation imaging apparatus according to claim 6, wherein based on the attenuation characteristic information, the reconstructing unit is configured to set the different radiation energies for the respective materials so that contrast between the plurality of materials exceeds a set base value.

8. The radiation imaging apparatus according to claim 1, wherein the analyzing unit analyzes the reconstructed image and obtains the evaluation information related to contrast between the plurality of materials.

9. The radiation imaging apparatus according to claim 8, wherein the evaluation information includes contrast obtained from a difference between average values of pixel values in regions of interest of the plurality of materials.

10. The radiation imaging apparatus according to claim 9, wherein the evaluation information includes a contrast to noise ratio obtained as a ratio between the contrast and a standard deviation of pixel values in the region of interest of one of the plurality of materials.

11. The radiation imaging apparatus according to claim 8, wherein the analyzing unit is configured to set the different radiation energies for the respective materials so that the evaluation information has a maximum value.

12. The radiation imaging apparatus according to claim 8, wherein the reconstructing unit is configured to generate the reconstructed image based on the different radiation energies whose settings have been changed, and the analyzing unit is configured to perform repetitive calculation of the evaluation information based on the reconstructed image.

13. The radiation imaging apparatus according to claim 12, wherein the analyzing unit is configured to determine whether the evaluation information obtained through the repetitive calculation has converged, and when the evaluation information has converged, the reconstructing unit is configured to determine radiation energies used in the calculation of the evaluation information that has converged as the different radiation energies for the respective materials.

14. The radiation imaging apparatus according to claim 1, wherein at least one of (a) the one or more processors connected to the one or more memories storing a program including instructions executed by the one or more processors and (b) the circuitry configured to function as an obtaining unit configured to obtain a plurality of radiation images that have been captured by a radiation detecting apparatus through a single radiation irradiation from a radiation generating unit.

15. The radiation imaging apparatus according to claim 14, wherein at least one of (a) the one or more processors connected to the one or more memories storing a program including instructions executed by the one or more processors and (b) the circuitry configured to function as a generating unit configured to generate material characteristic images of the materials using the different radiation energies, wherein the obtaining unit is configured to obtain the plurality of radiation images that have been captured by the radiation detecting apparatus as a plurality of radiation images based on the different radiation energies, and the generating unit is configured to generate the material characteristic images based on the plurality of radiation images obtained by the obtaining unit.

16. The radiation imaging apparatus according to claim 6, wherein the storing unit is configured to hold a table in which information of a subject is associated with the different radiation energies for the respective materials, and with reference to the table, the reconstructing unit is configured to set the different radiation energies for the respective materials associated with the information of the subject to be captured.

17. The radiation imaging apparatus according to claim 16, wherein the information of the subject includes information of a body thickness of the subject or information of thicknesses of the materials.

18. A radiation imaging apparatus, comprising at least one of (a) one or more processors connected to one or more memories storing a program including instructions executed by the one or more processors and (b) circuitry configured to function as:

an extracting unit configured to extract materials included in a radiation image that has been captured using different radiation energies;

a reconstructing unit configured to generate a reconstructed image by compositing monochromatic radiation images of the different radiation energies for of the materials; and an analyzing unit configured to analyze the reconstructed image to obtain evaluation information by comparing information related to pixel values in regions of interest of the materials, wherein the reconstructing unit generates a new reconstructed image by compositing new monochromatic radiation images of different radiation energies changed using the evaluation information.

19. The radiation imaging apparatus according to claim 1, further comprising a display controlling unit configured to cause a displaying unit to display the reconstructed image, wherein the display controlling unit is configured to cause the displaying unit to display a user interface that continuously changes settings of the different radiation energies together with the displayed reconstructed image.

20. A radiation imaging apparatus, comprising at least one of (a) one or more processors connected to one or more memories storing a program including instructions executed by the one or more processors and (b) circuitry configured to function as:

a reconstructing unit configured to generate a reconstructed image by compositing monochromatic radiation images of different radiation energies, the monochromatic radiation images being obtained using material characteristic images of the materials generated by performing energy subtraction using radiation distribution information pieces corresponding to different radiation energies; and an analyzing unit configured to analyze the reconstructed image to obtain evaluation information by comparing information related to pixel values in positions of materials, wherein the reconstructing unit generates a new reconstructed image by compositing new monochromatic radiation images of different radiation energies changed using the evaluation information.

21. A radiation imaging method, comprising the steps of:

generating monochromatic radiation images of different radiation energies for materials using material characteristic images of the materials generated by performing energy subtraction using radiation distribution information pieces corresponding to different radiation energies;

generating a reconstructed image by compositing the monochromatic radiation images;

analyzing the reconstructed image to obtain evaluation information by comparing information related to pixel values in regions of interest of the materials; and generating a new reconstructed image by compositing new monochromatic radiation images of different radiation energies changed using the evaluation information.

22. A radiation imaging method, comprising the steps of:

extracting materials included in a radiation image that has been captured using different radiation energies;

generating a reconstructed image by compositing monochromatic radiation images of the different radiation energies for the materials;

analyzing the reconstructed image to obtain evaluation information by comparing information related to pixel values in regions of interest of the materials; and generating a new reconstructed image by compositing new monochromatic radiation images of different radiation energies changed using the evaluation information.

23. A radiation imaging method, comprising the steps of:

generating a reconstructed image by compositing monochromatic radiation images of different radiation energies, the monochromatic radiation images being obtained using material characteristic images of the materials generated by performing energy subtraction using radiation distribution information pieces corresponding to different radiation energies;

analyzing the reconstructed image to obtain evaluation information by comparing information related to pixel values in positions of materials; and generating a new reconstructed image by compositing new monochromatic radiation images of different radiation energies changed using the evaluation information.

24. A non-transitory computer-readable storage medium storing a program for causing a computer to execute the radiation imaging method according to claim 21.

25. A non-transitory computer-readable storage medium storing a program for causing a computer to execute the radiation imaging method according to claim 22.

26. A non-transitory computer-readable storage medium storing a program for causing a computer to execute the radiation imaging method according to claim 23.

* * * * *